United States Patent [19]
O'Lenick, Jr.

[11] Patent Number: 5,646,321
[45] Date of Patent: Jul. 8, 1997

[54] GUERBET MEADOWFOAM ESTERS

[75] Inventor: Anthony J. O'Lenick, Jr., Lilburn, Ga.

[73] Assignee: Siltech Inc., Norcross, Ga.

[21] Appl. No.: 516,138

[22] Filed: Aug. 17, 1995

[51] Int. Cl.$^6$ ............................................. C07C 57/00
[52] U.S. Cl. ............................................. 554/224; 554/170
[58] Field of Search ............................. 554/223, 224, 554/170

Primary Examiner—Deborah D. Carr

[57] ABSTRACT

The present invention deals with the certain novel esters which are prepared by the reaction of a guerbet alcohol and meadowfoam fatty, methyl ester or triglyceride. These materials are useful as cosmetic ingredients where outstanding liquidity, resistance to oxidation, and minimal taste and odor variation are required. This combination of properties make these compounds excellent candidates as additives to personal care products like skin care oils and lipsticks.

14 Claims, No Drawings

GUERBET MEADOWFOAM ESTERS

BACKGROUND OF THE INVENTION

1. Field of the Invention

The present invention deals with the certain novel esters which are prepared by the reaction of a guerbet alcohol and meadowfoam fatty, methyl ester or triglyceride. These materials are useful as cosmetic ingredients where outstanding liquidity, resistance to oxidation, and minimal taste and odor variation are required. This combination of properties make these compounds excellent candidates as additives to personal care products like skin care oils and lipsticks.

2. Description of the Art Practices

Guerbet alcohols have been known for many years. Over the years there have been a number of derivatives patented. U.S. Pat. No. 4,868,236 to O'Lenick discloses a guerbet citric ester and polymers thereof useful in plastic lubrication.

U.S. Pat. No. 4,425,458 to Lindner and O'Lenick teaches that specific guerbet esters can be used as polycarbonate lubricants.

The selection of an ester for use in pigmented products requires that there be a significant number of carbon atoms present to get the wetting and oily properties desired. Fatty esters of guerbet alcohols and saturated fatty acids results in the preparation of esters which are liquid but not sufficiently hydrophobic (that is they do not have enough carbon atoms present) or if there are enough carbon atoms present, the products are slushy or solid at ambient temperatures.

Selecting unsaturated acids, like oleic acid, to make guerbet esters results in the desired liquidity, but two additional problems are encountered, (a) there is not enough hydrophobicity since the number of carbon atoms is limited to 18, and (b) the acid undergoes pronounced degradation in a process referred to as "rancidity", making them unacceptable for applications where odor and taste is an issue. The recent availability of meadowfoam oil, with it's 20 to 22 carbon atoms and the specific location of it's double bonds, and it's reaction with the regiospecific beta branch of guerbet alcohols results in the preparation high molecular weight liquid stable ester, acceptable for use in pigmented personal care applications, like make-up and lipstick.

None of the prior compounds possess the critical meadowfoam carboxy moiety combined with the guerbet linkage in the molecule. Molecules of the current invention have guerbet substitution patterns in the alcohol and the meadowfoam alkyl group in the acid portion of the molecule.

THE INVENTION

This invention relates to a particular group of highly branched, unsaturated esters made by the reaction of a guerbet alcohol and meadowfoam oil, meadowfoam methyl ester or meadowfoam fatty acid. The terms meadowfoam oil, fatty acid or methyl ester as used herein refer to a specific alkyl distribution of the groups which is are native to a plant limnathes Alba, commonly called meadowfoam oil. Meadowfoam oil is harvested from a plant and sold commercially by The Fanning Corporation under the tradename "Fancor Meadowfoam".

The unique structure of the oil coupled with the proper selection of the guerbet alcohol chosen to make the ester results in a liquid ester with oxidative stability heretofore unattainable. The fatty distribution of the oil ranges from 20 to 22 carbons and has unsaturation in specific locations. The oil contains 97% by weight higher unsaturated alkyl groups. Typically, meadowfoam oil contains 60–65% of a twenty carbon mono-carboxy acid having one unsaturation between carbon 5 and 6. Additionally, it contains 12–20% of a twenty two carbon mono-carboxy acid having one unsaturation between either carbon 5 and 6, or carbon 13 and 14 and 15–28% of a twenty two carbon mono-carboxy acid having one unsaturation between both carbon 5 and 6, or carbon 13 and 14. The combination of the fact that there are 20 to 22 carbon atoms in the group leads to lack of volatility, the presence of unsaturation leads to liquidity and the fact that the di-unsaturated moieties are not conjugated leads to outstanding oxidative stability.

Additional aspects of the invention is the application of these materials as personal care applications were the specific properties of an ester having a guerbet derived branching on the alcohol portion of the molecule and the unique distribution of the meadowfoam on the other result in superior liquidity, lubricity, and outstanding oxidative stability.

The compounds of the current invention are specific guerbet alcohol/meadowfoam esters conforming to the following structure;

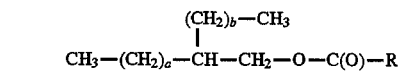

wherein

R is

60–65% by weight —$(CH_2)_3$—$CH=CH$—$(CH_2)_{13}$—$CH_3$

12–20% by weight a mixture of

—$(CH_2)_3$—$CH=CH$—$(CH_2)_{15}$—$CH_3$ and

—$(CH_2)_{11}$—$CH=CH$—$(CH_2)_7$—$CH_3$ and

15–28% by weight

—$(CH_2)_3$—$CH=CH$—$(CH_2)_6$—$CH=CH$—$(CH_2)_6$—$CH_3$;

a and b are independently integers ranging from 4 to 20.

PREFERRED EMBODIMENT

In a preferred embodiment a and b are each 8.

In another preferred embodiment a, b are each 6.

In another preferred embodiment a, b are each 4.

In still another preferred embodiment a, b are each 10.

In another preferred embodiment a, b are each 20.

The invention also teaches that an ester can be made by the esterification reaction of a guerbet alcohol conforming to the following structure;

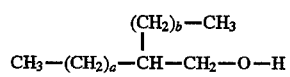

a and b are independently integers ranging from 4 to 20; and meadowfoam oil.

In a preferred embodiment the esterification is conducted at a temperature of between 150 and 210 C.

In another preferred embodiment the esterification is conducted using stannous oxylate as a catalyst.

EXAMPLES

RAW MATERIALS
Guerbet Alcohols

Guerbet Alcohols are regiospecifically beta branched alcohols. They have been known since the 1890's when Marcel Guerbet first synthesized them. (M. Guerbet, C. R. Acad. Sci. Paris, 128, 511; 1002 (1899)). These materials are high in molecular weight and are liquid to very low temperatures. The guerbet reaction gives very specific branching in the alcohol as shown;

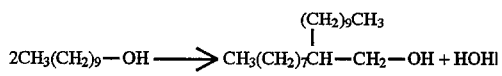

As can be seen by the above reaction the molecules have substitution on the second carbon from the hydroxyl group. This branching has been found to be critical to the preparation of a product having the desired lubrication and oxidative stability properties. If the branching were on the same carbon as the hydroxyl group, the hydroxyl group would be a secondary one and would be very hindered and has low reactivity. As one moves the branch position away from the beta carbon, the liquidity, lubricity and metal substantivity decreases. If the branch is lower alkyl like methyl in some oxo alcohols, there is little increase in the liquidity, lubricity and metal substantivity over normal alcohols having the same number of carbons. Additionally, the oxo process gives only some beta branching ( between 1 and 28%) the guerbet process gives essentially 100% product.

Guerbet alcohols that are the reaction product of one specific raw material alcohol will result in a so called "homo-guerbet". In this case R and R' are identical. If the starting alcohols used in the guerbet reaction are of differing molecular weights a so called "hetero-guerbet" results. This type o guerbet has a mixed distribution of all possible combinations of alcohols. For this reason R and R' in the generic formula may be the same or different.

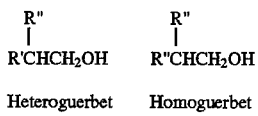

Heteroguerbet      Homoguerbet

Guerbet alcohols are available commercially from Nova Molecular Technologies Janesville, Wis. They are marketed under the following commercial names:

| Example | Commercial Name | a | b |
|---|---|---|---|
| 1 | Nova Guerbet C10 | 3 | 3 |
| 2 | Nova Guerbet C12 | 4 | 4 |
| 3 | Nova Guerbet C14 | 5 | 5 |
| 4 | Nova Guerbet C16 | 6 | 6 |
| 5 | Nova Guerbet C18 | 7 | 7 |
| 6 | Nova Guerbet C20 | 8 | 8 |
| 7 | Nova Guerbet C32 | 14 | 14 |

Meadowfoam Oil

Meadowfoam Oil can be used as a triglyceride, which is the oil as provided, reacted with methanol in processes known to those skilled in the art to make methyl ester, or reacted using technology known in the art to make carboxylic acids. The CAS number of meadowfoam oil is 153065-40-8.

The choice of triglyceride, acid or methyl ester does not change the structure of the resultant ester. It does however change the by-product produced. In the case of the triglyceride, glycerine is produced, in the case of the acid water is produced and in the case of the methyl ester methanol is produced.

Ester Synthesis

The esterification reaction is carried out using an excess of alcohol or meadowfoam or more typically using an equivalent of each. The esterification reaction can be carried out with or without catalyst, however when no catalyst is used the reaction times are protracted. Catalysts like benzene sulfonic acid, tin, sulfuric acid, tin salts and the like can be used. The most satisfactory catalyst is stannous oxylate.

General Procedure—Meadowfoam Oil

To the specified number of grams of guerbet alcohol (examples 1–7) is added then 354.0 grams of the meadowfoam oil. Next add 0.1% stannous oxylate based upon the total weight of the batch after all ingredients have been charged, under agitation. The temperature of the mass is raised to 150°–200° C. and glycerine is stripped off under vacuum. The acid value and hydroxyl value drop to vanishingly small values, and the saponification value increases to theoretical.

The products are clear liquids and are liquid to extraordinary temperatures. They exhibit outstanding lubrication properties and are outstanding viscosity index modifiers.

| | Guerbet Alcohol | |
|---|---|---|
| Example | Example | Grams |
| 8 | 1 | 157.0 |
| 9 | 2 | 185.0 |
| 10 | 3 | 213.0 |
| 11 | 4 | 241.0 |
| 12 | 5 | 269.0 |
| 13 | 6 | 297.0 |
| 14 | 7 | 465.0 |

General Procedure—Meadowfoam Oil

To the specified number of grams of guerbet alcohol (examples 1–7) is added then 354.0 grams of the meadowfoam fatty acid. Next add 0.1% stannous oxylate based upon the total weight of the batch after all ingredients have been charged, under agitation. The temperature of the mass is raised to 180°–200° C. and water is stripped off under vacuum. The acid value and hydroxyl value drop to vanishingly small values, and the saponification value increases to theoretical.

The products are clear liquids and are liquid to extraordinary temperatures. They exhibit outstanding lubrication properties and are outstanding viscosity index modifiers.

| | Guerbet Alcohol | |
|---|---|---|
| Example | Example | Grams |
| 15 | 1 | 157.0 |
| 16 | 2 | 185.0 |
| 17 | 3 | 213.0 |
| 18 | 4 | 241.0 |
| 19 | 5 | 269.0 |

-continued

| | Guerbet Alcohol | |
|---|---|---|
| Example | Example | Grams |
| 20 | 6 | 297.0 |
| 21 | 7 | 465.0 |

Liquid products which contain unsaturation are subject to an oxidation process referred to as rancidity. The double bond (conjugated or unconjugated) present for the desired liquidity is oxidized to aldehydes and ketones which react to form compounds causing bad color, odor and taste. In many applications including lipsticks, mal odor and mal taste are major problems, but liquidity and hydrophobicity and liquidity are desired. The presence of the aldehydic rancidity by-products produce unacceptable odor, color and taste components have a profound effect upon these properties at very minute concentrations. Studies have shown that the part per billion levels of some aldehydic compounds cause unacceptable properties.

RANCIDITY TESTING

Rancidity was tested using gas chromotography on the head space above the product stored at specific conditions looking for degradation products. (Addition of 5 grams product to be tested to a 100 ml bottle equipped with a rubber septum top stored for 3 months)

Temperature 20 C.

| Material | Aldehyde (Head Space analysis) | Odor | Taste |
|---|---|---|---|
| Example 12 | None Detected | Good | Good |
| Example 20 | None Detected | Good | Good |
| Example 11 | None Detected | Good | Good |
| | Unsaturated Compounds | | |
| Oleic acid - Guerbet 20 Ester | 80 ppm | Fair | Fair |
| Oleic Acid Guerbet 16 ester | 100 ppm | Unacceptable | Fair |
| Tridecyl Oleate | 90 ppm | Fair | Fair |
| TMP Trioleate | 120 ppm | Unacceptable | Unacceptable |

Temperature: 50 C.

| Material | Aldehyde (Head Space) | Odor | Taste |
|---|---|---|---|
| Example 12 | None Detected | Good | Good |
| Example 20 | None Detected | Good | Good |
| Example 11 | None Detected | Good | Good |
| | Unsaturated Compounds | | |
| Material | Aldehyde (Head Space analysis) | Odor | Taste |
| oleic acid C-20 Guerbet ester | 200 ppm | Unacceptable | Unacceptable |

| Oleic Acid C-16 Guerbet ester | 175 ppm | Unacceptable | Fair |
| Tridecyl Oleate | 220 ppm | Unacceptable | Unacceptable |
| TMP Trioleate | 210 ppm | Unacceptable | Unacceptable |

Oleic Acid/C-20 Guerbet ester is the reaction product of (Raw material example 6) and oleic acid.
Oleic Acid/C-16 Guerbet ester is the reaction product of (Raw material example 4) and oleic acid.
TMP trioleate is trimethylol propane tri oleate and is an item of commerce.

I claim:
1. An ester which conforms to the following structure:

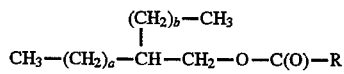

wherein:
R is
60–65% by weight —$(CH_2)_3$—CH=CH—$(CH_2)_{13}$—$CH_3$
12–20% by weight a mixture of

—$(CH_2)_3$—CH=CH—$(CH_2)_{15}$—$CH_3$ and

—$(CH_2)_{11}$—CH=CH—$(CH_2)_7$—$CH_3$ and
15–28% by weight

—$(CH_2)_3$—CH=CH—$(CH_2)_6$—CH=CH—$(CH_2)_6$—$CH_3$;

a, b, c and d are independently integers ranging from 4 to 20.
2. An ester of claim 1 wherein a and b are each 8.
3. An ester of claim 1 wherein a, b are each 6.
4. An ester of claim 1 wherein a, b are each 4.
5. An ester of claim 1 wherein a, b are each 10.
6. An ester of claim 1 wherein a, b are each 20.
7. An ester made by the esterification reaction of a guerbet alcohol conforming to the following structure;

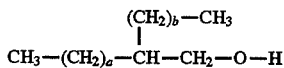

a and b are independently integers ranging from 4 to 20; and meadowfoam oil.
8. An ester of claim 7 wherein said esterification is conducted at a temperature of between 150° and 210° C.
9. An ester of claim 7 wherein said esterification is conducted using stannous oxylate as a catalyst.
10. An ester of claim 7 wherein a and b are each 8.
11. An ester of claim 7 wherein a, b are each 6.
12. A ester of claim 7 wherein a, b are each 4.
13. A ester of claim 7 wherein a, b are each 10.
14. A ester of claim 7 wherein a, b are each 20.

* * * * *